United States Patent

Lerner

[11] Patent Number: 5,879,699
[45] Date of Patent: Mar. 9, 1999

[54] MEDICATION DISPENSING SYSTEM

[76] Inventor: Julie Beth Green Lerner, 12437 N. 80th Pl., Scottsdale, Ariz. 85260

[21] Appl. No.: 868,432

[22] Filed: Jun. 3, 1997

[51] Int. Cl.[6] ....................................................... A61K 9/68
[52] U.S. Cl. ........................................... 424/440; 424/439
[58] Field of Search ..................... 424/439, 449, 424/424, 425; 426/100, 101, 104, 111

[56] References Cited

U.S. PATENT DOCUMENTS 5,176,151  1/1993  Harding ................................. 128/842
5,525,351  6/1996  Dam ...................................... 424/440
5,525,352  6/1996  Kontos et al. ......................... 424/440
5,567,439  10/1996 Myers et al. .......................... 424/486

*Primary Examiner*—Thurman K. Page
*Assistant Examiner*—Kathryne E. Shelborne
*Attorney, Agent, or Firm*—Gregory J. Nelson

[57] ABSTRACT

A hollow, consumable fillable dispenser having a filler tube for delivery of medication in a more palatable manner. The dispenser may be a hard or chewy confection and defines a hollow chamber which may be filled with a medication at time of use by means of the filler tube.

13 Claims, 1 Drawing Sheet

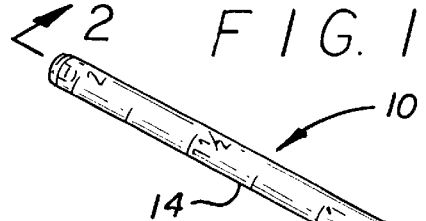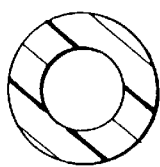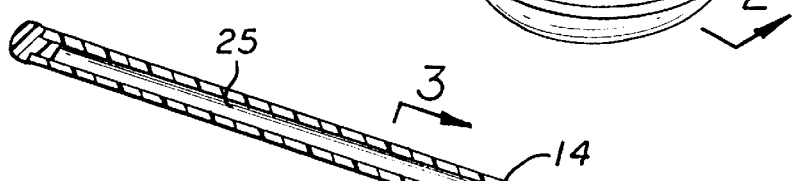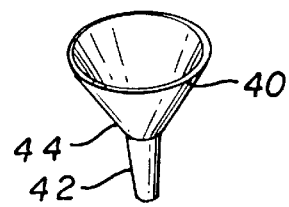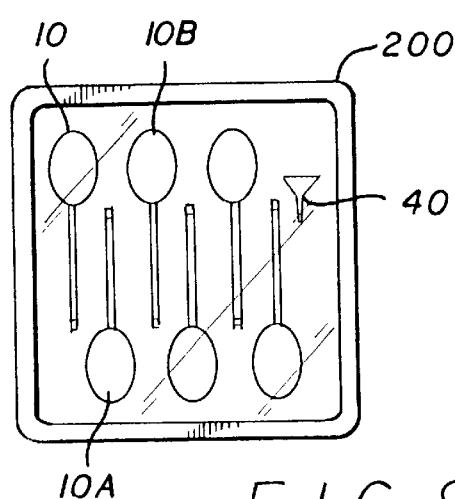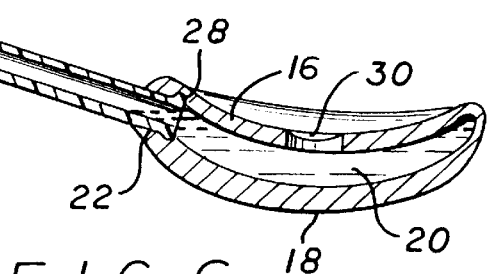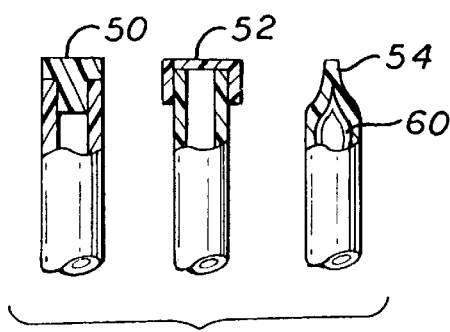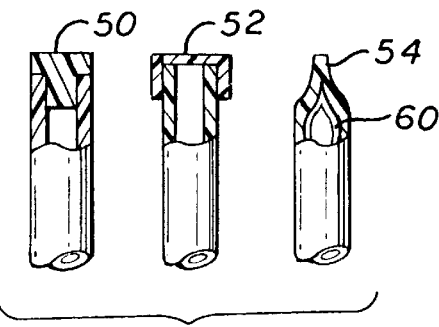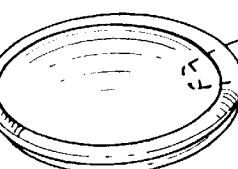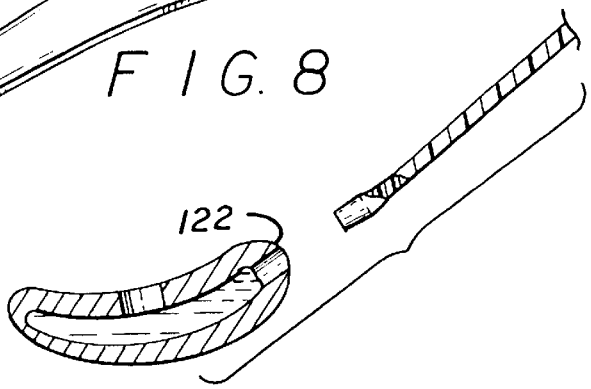

5,879,699

MEDICATION DISPENSING SYSTEM

BACKGROUND OF THE INVENTION

Field of the Invention

The present invention relates to a medication dispensing system and more particularly relates to a system having a consumable dispenser which contains the medication and which is consumed by the user to deliver the medication. More particularly, the invention relates to a dispenser which encourages persons who dislike medication to take medication.

It is difficult for many persons to take medications and the problem is particularly acute in the case of small children and the elderly. Children as well as many adults resist taking medication and thus lose the beneficial effects of the medication. Children may refuse to swallow the medication or will simply expel it when administered.

Accordingly, there is a need for a device that will make the taking of medications more palatable and a more pleasant experience so that both adults and children receive the beneficial effects of the medication by properly and timely receiving the medication in the prescribed amounts.

The patent literature discloses various devices for this purpose including the following: U.S. Pat. Nos. 4,419,911; 5,223,259; 5,490,989 and 5,288,498. These patents generally all relate to medication delivery systems having a stick and a means for securing medication to the end of the stick. In these patents, the drug or medication is contained within some type of a matrix at the end of the stick. The matrix may be a candy which contains the medicine or may be another type of containment device such as a membrane or a screen. However, while the devices shown in the foregoing patents may be helpful in delivering medication in certain situations, they are not of a type that can be selectively filled by the user or a parent at the time the medication is to be dispensed.

Accordingly, there is a need for a device which can be filled with a selected medication at the time of use and which device will make the administration of medication more palatable, disguising the flavor or taste which many persons find objectionable. Thus making the taking of medication a less objectionable and perhaps a pleasant experience.

BRIEF SUMMARY OF THE INVENTION

Briefly, in a preferred embodiment the present invention is directed to a hollow, consumable dispenser attached to a filler tube. The fillable dispenser is dissolvable and consumable and may be a confection such as a hard candy having a hollow center or may be a chewy candy such as gum drops with a honey type ingredient which soothes sore throats which often accompany illness. An opening is provided in the dispenser which opening receives the hollow filler tube. Preferably the filler tube is a soft, bendable or pliable material and the filler tube has an end through which medication may be delivered to the center of the consumable dispenser. A device, to assist in filling the dispenser with medication such as a funnel may be provided either as a separate or an integral part of the dispenser to assist in the filling operation making it simpler and convenient. Once the hollow center of the dispenser has been filled with the appropriate medication, the end of the filler tube may be closed by twisting or by placing a cap or plug over the distal end. Preferably, the dispenser component has a section which will dissolve more quickly than the remainder of the dispenser so that the medication is quickly and immediately discharged when first placed in the mouth of the patient.

The device is a single-use device and may be provided in various flavors and a plurality of such devices may be provided in a sealed package to the consumer. As indicated, a funnel or other filling device would also be provided to assist the user or adult in filling the dispenser.

The medication system may also be pre-filled with the medication.

BRIEF DESCRIPTION OF THE DRAWINGS

The above and other objects and advantages of the present invention will become more apparent from the following description, claims and drawings in which:

FIG. 1 is a perspective view of the medication dispenser of the present invention;

FIG. 2 is a longitudinal cross-sectional view of the dispenser shown in FIG. 1;

FIG. 3 is a cross-sectional view of the filler tube taken along line 3—3 of FIG. 2;

FIG. 4 is a perspective view of a funnel which may be used to assist in the filling of the dispenser of the present invention;

FIG. 5 is a plan view of a plurality of dispensing devices and associated funnel packaged for distribution to consumers;

FIG. 6 is a view showing three alternate arrangements for the open or distal end of the filler tube;

FIG. 7 is a perspective view of an alternate embodiment of the present invention;

FIG. 8 is a cross-sectional view of the dispenser and lower end of the filler tube; and FIG. 9 is a perspective view of an alternate embodiment of the invention showing the end of the filler having an integrally formed funnel.

Turning now to the drawings, particularly FIGS. 1 to 4 and 6, the dispenser of the present invention is generally designated by the numeral 10 and has dispenser 12 and a filler tube 14 which also serves as a handle for the dispenser. The dispenser 12 may be variously configured but preferably has a shape and size that is comfortable in the mouth of the user. Adult and pediatric sizes may be provided. As shown the dispenser has the general shape of a spoon with an upper concave surface 16 and a slightly convex lower surface 18 so that it is comfortable when it is placed in the user's mouth. The dispenser is sized approximately corresponding to the size of an ordinary teaspoon. The upper and lower surfaces 16 and 18 define a hollow interior 20 and access opening 22 is provided at one side or end of the dispenser. The access opening 22 receives the filler tube 14. Tube 14 may be of any suitable and safe material such as a bendable or pliable plastic. The tube 14 defines an hollow lumen or passageway 25. The inner or proximal end of the filler tube may be provided with an enlarged lip 28 which serves to assist in maintaining the tube in place. In the manufacture of the dispensing system, the dispenser is formed as by molding, dipping or casting the dispenser to form it on the proximal end of the filler tube so that the two are integrally attached.

Preferably the dispenser is made from a suitable food confection such as a hard candy or chewy candy such as gumdrops and cough drops. A chewy candy is more appropriate for children while adults, particularly the elderly, may prefer a harder confection which can be slowly dissolved in the user's mouth. Accordingly, the dispenser can be made of conventional ingredients such as sugar or sugar syrup, water and selected flavorings which are allowed to crystallize and harden into the desired shape. The confection may also include honey or other ingredients which may help to soothe the throat of the user. Preferably, an area 30 of the dispenser is formed in a manner so that it will dissolve more quickly than the remainder of the dispenser, thereby quickly dispensing the medication contained in the hollow center 20 within the patient's mouth. The area 30 may be thinner or may be of a second faster dissolving material. The flavor of the confection will help to disguise the medication and make it more palatable so that the patient will swallow and expel the medication.

Section 30 as indicated, will dissolve more quickly than the remainder of the dispenser. Therefore, if the user does not consume all of the dispenser, the medication will nevertheless be released into the patient's mouth and the user may dispose of the remainder of the dispenser.

The dispenser is filled by pouring the desired medication, such as a liquid cough syrup or cough suppressant, through the hollow lumen 25 of the tube 14. The distal end of the tube is designed to accept a funnel 40 of conventional shape having a spout 42. Thus, the spout 42 may be placed in engagement with the open, distal end of the filler tube 14 and the prescribed amount of the medication poured into the funnel. By properly holding the funnel and dispenser, gravity will cause the medication to flow through the lumen 25 to the hollow interior 20 of the dispenser. The funnel may be provided with indicia or calibrations 44 to assist in the user filling the interior with the proper amount or quantity of medication.

Once the dispenser has been filled, the distal end of the filler tube may be closed by the means shown in FIG. 6. A plug 50 may be inserted into the end of the tube to seal it. Alternatively, a cap 52 may be placed over the end of the filler tube. In still another alternate arrangement, the distal end of the sealer tube may be crimped or twisted at 54 to close it. The interior of the filler tube may be provided with a section 60 near its end which is coated with a sticky food safe substance which may assist in retaining the tube in the crimped, sealed condition.

Once the dispenser has been filled and the end sealed, the dispenser is placed in the user's mouth which, due to the body temperature of the user, will cause the material of the dispenser to begin dissolving. As indicated, preferably a section 30 of the dispenser will dissolve more quickly, releasing the contents into the user's mouth. The flavor and general lollipop configuration of the device will make the device more appealing to those using the dispenser, particularly smaller children.

The dispenser may be prefilled with other substances such as a dentifrice or a breath enhancing agent of the user's choice to counteract halitosis. These substances are included with the broad term "medication" as used herein. In such instances, the dispenser is a chewable or dissolvable confection having a hollow center containing the appropriate substance. The user can conveniently carry a supply of the dispensers ready for use to freshen and clean the user's mouth. Since the dispenser may be consumed by either chewing or dissolved by sucking, the dispenser may be made of various confections, children will generally prefer a softer, gummy confection which may be chewed while an adult may prefer a harder candy.

FIG. 7 shows an alternate embodiment of the present invention generally designated by the numeral 100 which again has a dispenser 112 made from a dissolvable material, preferably a hard or chewy confection or candy. The interior of the dispenser again is hollow as shown in FIG. 8, defining a hollow center 120 for the containment of a medication. In this embodiment, the medication is pre-filled into the hollow center and the handle 114 secured in place by inserting and sealing it into the opening 122 in the dispenser.

In FIG. 5, a representative packaging system is shown. The package may include a backing sheet which is shown as generally rectangular of plastic or fiberboard 200. A plurality of individual dispensers 10 are arranged on the backing card 200 and are alternately arranged in juxtaposition for compactness. The system includes a funnel 40 all of which are provided to the consumer sealed onto the backing by conventional packaging methods such as shrink wrap.

In FIG. 8 the filler tube 214 is hollow and may be crimped at 220 once filled. In FIG. 9 the distal end of the filler tube 214 is formed having an integral funnel 250.

Accordingly, the present invention provides a novel medication system for the delivery of medications, particularly liquid medications. The system may be useful both for adults, specifically the elderly, and by parents and guardians when administering such medications to small children. In the preferred embodiment, the system is provided to the consumer so that it may be filled at the time of use. In other embodiments, the dispenser may be pre-filled with a dosage of medication and provided to the consumer in this form.

While the principles of the invention have been made clear in the illustrative embodiments set forth above, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

I claim:

1. A dispenser for a liquid medication comprising:
   a hollow filler tube having opposite first and second ends; and
   a dispenser secured to the second end of said tube, said dispenser defining a hollow interior communicating with said tube, said dispenser being substantially entirely of a consumable, dissolvable food material.

2. The dispenser of claim 1 wherein said dispenser is generally spoon-shaped.

3. The dispenser of claim 1 wherein said dispenser has an area which will dissolve more rapidly than the remaining portion of the dispenser.

4. The dispenser of claim 1 wherein said filler tube includes indicia for measuring the contents delivered through the filler tube.

5. The dispenser of claim 1 wherein a plurality of said dispensers are packaged to the consumer along with a filling device.

6. The dispenser of claim 1 wherein said filler tube is adapted to be crimped to a sealed condition.

7. The dispenser of claim 1 wherein said filler tube is generally cylindrical having a distal end which is funnel shaped.

8. The dispenser of claim 1 wherein said food material is a chewy substance.

9. The dispenser of claim 1 wherein said food material is a hard confection.

10. A delivery system for an ingestible medication comprising of a dispenser defining a hollow interior, said dispenser body having a body being substantially entirely a first consumable, dissolvable food material.

11. The dispenser of claim 10 wherein said dispenser body defines an area which will dissolve more rapidly that the remaining body material.

12. The dispenser of claim 11 wherein said area has a thinner cross sectional thickness than the remainder of the dispenser body.

13. The dispenser of claim 11 wherein said area comprises a second food material which dissolves more rapidly than said first food material.

* * * * *